US00PP25600P2

(12) United States Plant Patent
Nishikawa

(10) Patent No.: US PP25,600 P2
(45) Date of Patent: May 26, 2015

(54) ***DELOSPERMA* PLANT NAMED 'WOWDOY3'**

(50) Latin Name: *Delosperma cooperi*
Varietal Denomination: WOWDOY3

(71) Applicant: Koichiro Nishikawa, Katuta-Gun (JP)

(72) Inventor: Koichiro Nishikawa, Katuta-Gun (JP)

( * ) Notice: Subject to any disclaimer, the term of this patent is extended or adjusted under 35 U.S.C. 154(b) by 104 days.

(21) Appl. No.: 13/987,585

(22) Filed: Aug. 9, 2013

(51) Int. Cl.
*A01H 5/02* (2006.01)

(52) U.S. Cl.
USPC ..... Plt./422

(58) Field of Classification Search
CPC ..... A01H 5/02
USPC ..... Plt./422
See application file for complete search history.

(56) References Cited

PUBLICATIONS

CPVO, 2013.*

* cited by examiner

*Primary Examiner* — June Hwu
*Assistant Examiner* — Keith Robinson
(74) *Attorney, Agent, or Firm* — Penny J. Aguirre

(57) ABSTRACT

A new cultivar of *Delosperma* plant, 'WOWDOY3', characterized by its compact and horizontal plant habit, its very floriferous and long blooming flowering habit, and its large flowers with petals that are orange on the outer region and yellow towards the center of the flower surrounding yellow petaloids.

2 Drawing Sheets

Botanical classification: *Delosperma cooperi.*
Variety denomination: 'WOWDOY3'.

CROSS REFERENCE TO RELATED APPLICATIONS

This application is co-pending with U.S. Plant Patent Applications filed for plants derived from the same breeding program that are entitled *Delosperma* Plant Named 'WOWDRY1' (U.S. Plant patent application Ser. No. 13/987,588), *Delosperma* Plant Named 'WOW2011-1' (U.S. Plant patent application Ser. No. 13/987,575), *Delosperma* Plant Named 'WOWDAY2' (U.S. Plant patent application Ser. No. 13/987,587), *Delosperma* Plant Named 'WOWDRW5' (U.S. Plant patent application Ser. No. 13/987,584), and *Delosperma* Plant Named 'WOWDW7' (U.S. Plant patent application Ser. No. 13/987,577).

BACKGROUND OF THE INVENTION

The present invention relates to a new and distinct cultivar of *Delosperma* plant, botanically known as *Delosperma cooperi* 'WOWDOY3' and will be referred to hereinafter by its cultivar name, 'WOWDOY3'. The new cultivar of *Delosperma* is an herbaceous perennial grown for container and landscape use.

The new cultivar was derived from a controlled breeding program conducted by the Inventor in Katsuta-Gun, Okayama-Pref., Japan. The overall purpose of the breeding program was to develop new cultivars of *Delosperma* plants with low-growing and well-spreading growth habits combined with long flowering periods and a unique range of flower colors.

'WOWDOY3' was selected in the Inventor's trial garden in summer of 2011 as a single unique plant from amongst the seedlings derived from self crossing an unnamed plant from the Inventor's breeding program, ref. code HANADOY1002, in summer of 2010.

Asexual propagation of the new cultivar was first accomplished by softwood stem cuttings in summer of 2011 by the Inventor in Katsuta-Gun, Okayama-Pref., Japan. Asexual propagation by softwood stem cuttings has determined the characteristics of the new cultivar are stable and reproduced true to type in successive generations.

SUMMARY OF THE INVENTION

The following traits have been repeatedly observed and are determined to be the characteristics of the new cultivar. These attributes in combination distinguish 'WOWDOY3' as a unique cultivar of *Delosperma.*

1. 'WOWDOY3' exhibits a compact and horizontal plant habit.
2. 'WOWDOY3' exhibits a very floriferous and long blooming flowering habit; blooming about 8 months.
3. 'WOWDOY3' exhibits large flowers with petals that are orange on the outer region and yellow towards the center of the flower surrounding yellow petaloids.

The parent plant of 'WOWDOY3', ref. code HANADOY 1002, differs from 'WOWDOY3' in having a taller plant habit and in having smaller flowers. 'WOWDOY3' can be most closely compared to the cultivar 'Jewel of Desert Garnet' (U.S. Plant Pat. No. 23,471). 'Jewel of Desert Garnet' differs from 'WOWDOY3' in having smaller flowers that are red with pink on the lower portion of the petals and pink petaloids, in having a shorter bloom period, and in having a shorter plant height. 'WOWDOY3' can also be compared to cultivars with co-pending patent applications from the same breeding program and are similar in plant height and in having large flowers.

'WOWDRY2' has flowers with petals that are red on the outer region and yellow towards the center of the flower surrounding yellow petaloids.

'WOWDRY1' has flowers with petals that are magenta pink on the outer region and yellow and white towards the center of the flower surrounding yellow and white petaloids.

'WOWDRW5' has flowers with petals that are magenta pink on the outer region and white towards the center of the flower surrounding white petaloids.

'WOWDW7' has flowers with white petals and white petaloids.

'WOW2011-1' has flowers with yellow petals and yellow petaloids.

BRIEF DESCRIPTION OF THE DRAWINGS

The accompanying colored photographs illustrate the overall appearance and distinct characteristics of the new *Delosperma*. The plant in the photograph is 3 months in age as grown in a 9-cm container in an unheated greenhouse in Noordwijkerhout, The Netherlands.

The photograph in FIG. 1 provides a side view of 'WOWDOY3' in bloom.

Figure 1:
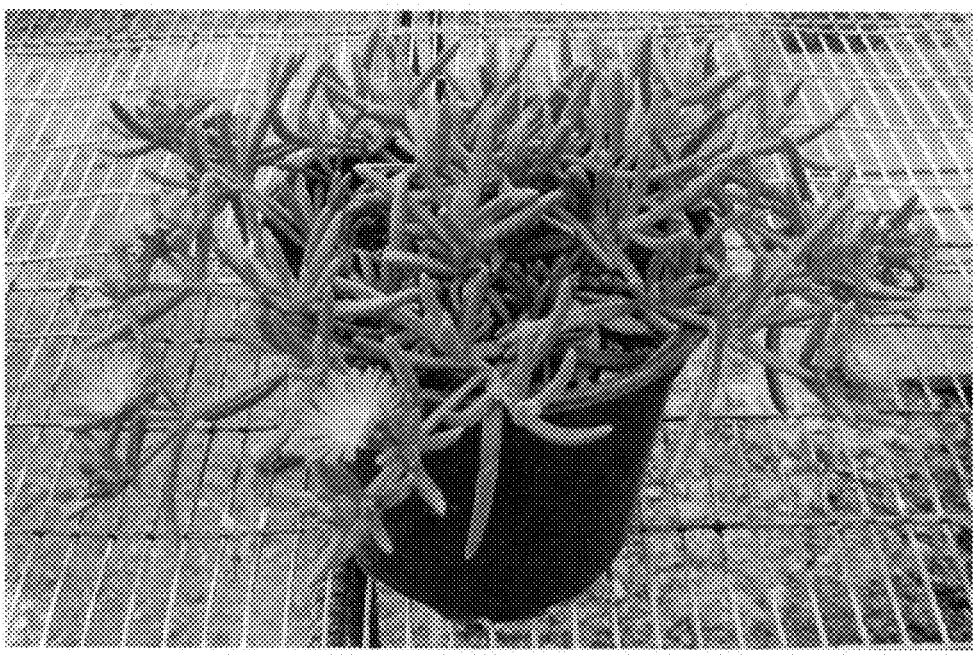
Figure 2:
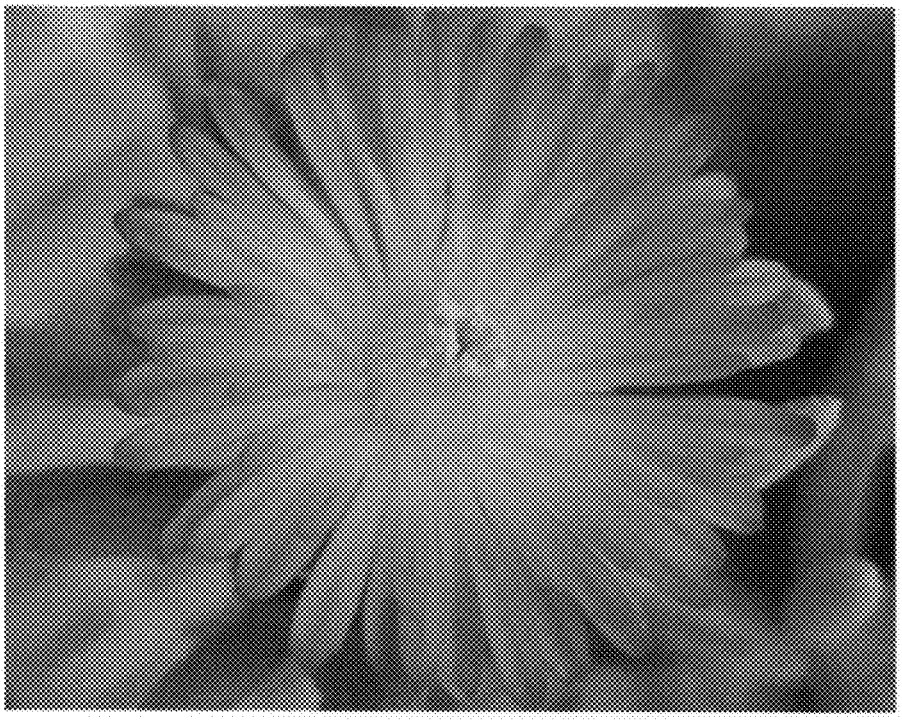

The photograph in FIG. 2 provides a close-up view of a flower of 'WOWDOY3'.

Figure 3:
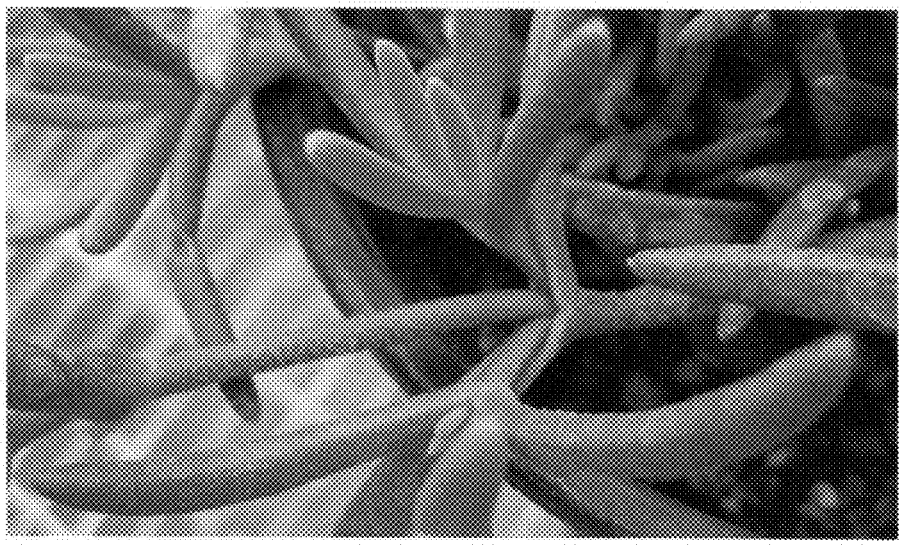

The photograph in FIG. 3 provides a close-up view of the foliage of 'WOWDOY3'.

The colors in the photographs may differ slightly from the color values cited in the detailed botanical description, which accurately describe the colors of the new *Delosperma*.

DETAILED BOTANICAL DESCRIPTION

The following is a detailed description of 3 months-old plants of the new cultivar as grown in 9-cm containers in an unheated greenhouse in Noordwijkerhout, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for about 8 weeks from spring into fall in Noordwijkerhout, The Netherlands.

*Plant type.*—Herbaceous perennial.

*Plant habit.*—Compact, well-spreading, prostrate.

*Height and spread.*—Reaches about 10 cm in height and about 22.3 cm in diameter.

*Cold hardiness.*—Observed to be hardy to U.S.D.A. Zone 7.

*Diseases.*—No more susceptible or resistant to diseases than other *Delosperma cooperi* varieties.

*Root description.*—Fibrous roots, primarily 161D in color.

*Propagation.*—Softwood stem cuttings.

*Growth habit.*—Moderate.

Stem description:

*Shape.*—Round.

*Stem color.*—Young stems a blend of 152D and strongly tinged with 180B, older stems 196C to 196D.

*Stem size.*—10 cm in length and 2 mm in diameter, branch internode length is 3.2 cm.

*Stem surface.*—Moderately glossy, moderately covered with very short glandular hairs; average of 0.2 mm in length, 155C in color.

*Branching habit.*—Freely branching, average of 15 lateral branches.

Foliage description:

*Leaf shape.*—Ligulate, triangular in diameter, succulent.

*Leaf division.*—Simple.

*Leaf base.*—Cuneate.

*Leaf apex.*—Acute.

*Leaf venation.*—No veins visible.

*Leaf margins.*—Entire.

*Leaf arrangement.*—Opposite.

*Leaf surface* (*upper and lower surface*).—Slightly glossy, slightly pubescent with very short glandular hairs, average length 0.2 mm, 157D in color.

*Leaf color.*—Young upper and lower surface; 138B.

*Leaf size.*—About 3 cm in length and 4 mm in width.

*Leaf quantity.*—Average of 10 per lateral branch (5 pairs).

*Leaf attachment.*—Sessile.

Inflorescence description:

*Inflorescence type.*—Flowers solitary, rotate.

*Flower number.*—Average of 1 per lateral stem.

*Flower fragrance.*—Moderately faint, sweet and pleasant.

*Flower aspect.*—Outward to upright.

*Flower longevity.*—Average of 4 days.

*Flower type.*—Single.

*Flower size.*—Average of 2.9 cm in diameter and 1.3 cm in depth.

*Flower buds.*—Broad ovate to oblong in shape, average of 8 mm in length and 6 mm in diameter, color; 143B to 143C, base 144C, surface texture is glabrous and glossy with sepal portion glabrous and matte.

*Sepals.*—5, ovate in shape, margin entire, average of 5 mm in length and 3 mm in width, broadly acute apex, broadly cuneate base, surface is smooth and matte on upper and lower surface, color; young upper and lower surface; 143B to 143C, base 144C, mature upper and lower surface; 143B to 143C.

*Petals.*—An average of 50 per flower, rotate and slightly curved arrangement, narrow oblanceolate in shape, surface smooth on upper and lower, margin entire, apex is obtuse, average of 1.2 cm in length and 1.5 mm in width, color opening upper surface; a blend of 25A and N25A, opening lower surface; N25A, lower half N25B, fully opened flowers upper surface; N25A to N25B, lower half 13B, base 4D, fully opened flowers lower surface; N25A to N25B, base 4D, non fading.

*Petaloid.*—Rotate and placed around stamens, average of 20, lanceolate in shape, margin entire, upper and lower surface glabrous and moderately to highly glossy, average of 5 mm in length and 0.75 mm in width, color upper and lower mature and immature surface; 15A, base 4D.

*Calyx.*—Rotate in shape, average of 6 mm in length and 1.2 cm in diameter.

*Peduncle.*—1.5 cm in length and 1.5 mm in diameter, held straight on top of lateral branch, color; 145C, slightly tinged 173C to 173D.

*Pedicel.*—None.

Reproductive organs:

*Pistils*.—About 5, average of 2 mm in length, triangular shaped stigma and N144A to N144B in color, style is an average of 2 mm in length and N144A to N144B in color, and ovary is 143C in color.

*Stamens*.—Average of 60, anthers are dorsifixed and narrow oblong in shape, average of 0.5 mm in length, filaments are 4 mm in length and NN155D in color, pollen is moderate to high in quantity and 6A in color.

*Fruit*.—Fruit and seed production was not observed under the conditions tested.

It is claimed:

1. A new and distinct variety of *Delosperma* plant named 'WOWDOY3' as described and illustrated herein.

* * * * *